United States Patent
Nöth et al.

[11] Patent Number: 5,808,070
[45] Date of Patent: Sep. 15, 1998

[54] PROCESS FOR PREPARING ALKALINE AMINOBOROHYDRIDES AND ALKALINE AMINOBOROHYDRIDE COMPLEXES

[75] Inventors: Heinrich Nöth; Steffen Thomas, both of Grünwald; Peter Rittmeyer, Sulzbach; Ulrich Wietelmann, Friedrichsdorf, all of Germany

[73] Assignee: Metallgesellschaft Aktiengesellschaft, Frankfurt/Main, Germany

[21] Appl. No.: 849,441

[22] PCT Filed: Nov. 16, 1995

[86] PCT No.: PCT/EP95/04500

§ 371 Date: Jun. 25, 1997

§ 102(e) Date: Jun. 25, 1997

[87] PCT Pub. No.: WO96/16066

PCT Pub. Date: May 30, 1996

[30] Foreign Application Priority Data

Nov. 18, 1994 [DE] Germany .......................... 44 41 064.6

[51] Int. Cl.⁶ ...................................................... C07F 5/02
[52] U.S. Cl. ............................. 546/13; 423/295; 548/110; 564/9
[58] Field of Search .................. 564/9; 546/13; 423/285

[56] References Cited

U.S. PATENT DOCUMENTS 5,466,798  11/1995  Singaram et al. ...................... 540/541
5,565,615  10/1996  Holzner et al. ............................ 564/9

*Primary Examiner*—Richard L. Raymond
*Attorney, Agent, or Firm*—Herbert Dubno

[57] ABSTRACT

A process is disclosed for preparing a compound of the Formula $$M(R^1R^2N.BH_3)$$

or a complex thereof of the Formula $$M(R^1R^2N.BH_3).xL$$

wherein

M is Li, Na, K, Rb or Cs;

$R^1$ is H, an aliphatic $C_1$ to $C_5$ residue, an aromatic residue, or a cycloaliphatic residue;

$R^2$ is H, an aliphatic $C_1$ to $C_5$ residue, an aromatic residue, or a cycloaliphatic residue; or $R^1$ and $R^2$ form a common cyclic residue;

L is a dipolar aprotic solvent; and x is a numerical value from 0.1 to 5, which comprises the steps of:

(a) where the compound of the Formula $M(R^1R^2N.BH_3)$ is prepared, reacting a compound of the Formula $$R^1R^2NH.BH_3$$

with an alkali metal or an alkali metal amide in a non-polar aliphatic or aromatic solvent; or (b) where the complex of the Formula $M(R^1R^2N.BH_3).xL$ is prepared, reacting the compound of the Formula $$R^1R^2NH.BH_3$$

with an alkali metal or an alkali metal amide in the dipolar, aprotic solvent or is a mixture of the dipolar aprotic solvent and the non-polar aliphatic or aromatic solvent.

8 Claims, No Drawings

PROCESS FOR PREPARING ALKALINE AMINOBOROHYDRIDES AND ALKALINE AMINOBOROHYDRIDE COMPLEXES

CROSS REFERENCE TO RELATED APPLICATION

This application is the U.S. National Phase of PCT/EP95/04500 filed 16 Nov., 1995.

BACKGROUND OF THE INVENTION

DESCRIPTION

This invention relates to a process for preparing alkaline aminoborohydrides and alkaline aminoborohydride complexes.

From the U.S. Pat. No. 2,999,864 metal derivatives of borohydride addition products are known. The preparation of these compounds is effected by reacting metal hydrides with borohydride addition products. For instance, lithium dimethylaminoborohydride should be accessible in the same way as sodium dimethylaminoborohydride through direct reaction of the corresponding alkali hydride with dimethylamineborane in dry ethylene glycol dimethyl ether. However, the publication by Keller, "Inorganic Chemistry" (1975), Vol. 14 (2), p. 140, discloses that the reaction of lithium hydride with dimeric dimethylamineborane at room temperature in diethyl ether will only lead to lithium dimethylaminoborohydride after several months reaction time. Whereas examinations by Hutchins et al, "Journal of Organic Chemistry" (1984), Vol. 49, p. 2438, confirm the smooth reaction of sodium hydride with dimethylamineborane in tetrahydrofuran to form sodium dimethylaminoborohydride, Singaram et al, Tetrahedron Letters (1992), Vol. 33, p. 4533, indicate that lithium aminoborohydrides can be prepared through reaction of n-butyllithium with amineborane addition products. The process proposed by Singaram is virtually restricted to the preparation of lithium aminoborohydrides, as only lithium alkyl compounds are stable and commercially available.

OBJECT OF THE INVENTION

As in the prior art non-uniform and in part contradictory statements are made with respect to the preparation of alkaline aminoborohydrides, it is the object underlying the invention to provide a process for preparing alkaline aminoborohydrides and their complex compounds from inexpensive raw materials, which provides high product yields within short reaction times and is suited for the preparation of a multitude of homologues.

SUMMARY OF THE INVENTION

The object underlying the invention is solved on the one hand by a process for preparing alkaline aminoborohydrides of the general formula $$M(R^1R^2N.BH_3)$$

by reacting an amineborane of the formula $$R^1R^2NH.BH_3$$

with an alkali metal or with an alkali amide in a nonpolar aliphatic or aromatic solvent, wherein M is Li, Na, K, Rb or Cs, $R^1$ is H, an aliphatic $C_1$—to $C_5$—residue, an aromatic residue or a cycloaliphatic residue, $R^2$ is H, an aliphatic $C_1$—to $C_5$—residue, an aromatic residue or a cycloaliphatic residue, and $R^1$ and $R^2$ is a common cyclic residue.

As alkali amides, the compounds $MNR^3R^4$ are used, where $R^3$ and $R^4$ are each H or an organic residue or the trimethylsilyl residue.

The process in accordance with the invention, which is performed at 0° to 100° C., thus yields alkaline aminoborohydrides by reacting addition products, which consist of borohydride and amines, with alkali metals or certain alkali compounds, which alkaline aminoborohydrides are generally hardly soluble in the nonpolar solvents, so that they are obtained as colourless, amorphous or crystalline precipitates. From the reaction mixtures the end products can either be obtained through solid-liquid separation or through evaporation of the solvent. The products are easy to handle, and they are in particular not self-igniting upon contact with air and/or water. The reaction generally takes place with a high yield of alkaline aminoborohydrides.

The object underlying the invention is on the other hand solved by a process for preparing alkaline aminoborohydride complexes of the formula $$M(R^1R^2N.BH_3).xL$$

by reacting an amineborane of the formula $$R^1R^2NH.BH_3$$

with an alkali metal or with an alkali amide, wherein the nonpolar aliphatic or aromatic solvent is replaced wholly or in part by a dipolar aprotic solvent, and wherein M is Li, Na, K, Rb or Cs, $R^1$ is H, an aliphatic $C_1$—to $C_5$—residue, an aromatic residue, or a cycloaliphatic residue, $R^2$ is H, an aliphatic $C_1$—to $C_5$—residue, an aromatic resdiue, or a cycloaliphatic residue, and $R^1$ and $R^2$ is a common cyclic residue, L is the dipolar aprotic solvent, and x is a numerical value from 0.1 to 5.

As alkali amides the compounds $MNR^3R^4$ are used, where $R^3$ and $R^4$ are each H or an organic residue or the trimethylsilyl residue.

The reaction is performed at temperatures between 0 and 100° C., preferably between 20 and 60° C. In the dipolar aprotic solvents the alkaline aminoborohydrides form defined complexes, which either isolated in solid form or directly in dissolved form can be used for organic syntheses. In some cases it is expedient to use mixtures from non-complexing (hexane, toluene) and complexing (dioxane, tetrahydrofuran) compounds as solvents, so as to operate in a homogeneous phase and reduce the content of the expensive complexing compounds.

In accordance with the invention it is particularly advantageous in some cases to perform the reaction with an alkali metal in the presence of a proton acceptor, where the proton acceptor acts as catalyst and adds the hydrogen formed during the reaction.

It turned out as particularly advantageous to use styrene as proton acceptor. The hydrogen formed during the reaction of the aminoborohydride addition product with an alkali metal hydrogenates the side chain of the styrene, which leads to an increased yield. As proton acceptor there can also be used butadiene, isoprene or similar dienes or polyenes.

In accordance with the invention it is furthermore advantageous to use hexane or toluene as nonpolar solvent. In these solvents, the alkaline aminoborohydrides are largely insoluble.

Furthermore, it is advantageous in accordance with the invention to use ether and/or tertiary amines, preferably tetrahydrofuran, diethyl ether, tetramethyl ethylenediamine or dioxane as dipolar aprotic solvent. These solvents lead to the formation of relatively stable and easy-to-handle complexes.

The process in accordance with the invention is particularly suited for the preparation of lithium dimethylaminoborohydride and the complexes of this compound, which can be used in the organic synthesis for the stereoselective reduction of $\alpha,\beta$-unsaturated carbonyl compounds to $\alpha,\beta$-unsaturated alcohols or for the conversion of aliphatic or aromatic amides to the corresponding alcohols or amines. Furthermore, esters, lactones, anhydrides, epoxides, oximes, acid chlorides, halides and nitrites can be reduced with lithium dimethylaminoborohydride and the complexes thereof.

The subject-matter of the invention will subsequently be explained with reference to several embodiments.

EXAMPLE 1

In a 2 l double-walled reactor 29.5 g (0.50 mol) dimethylaminoborane and 12.0 g (0.52 mol) lumpy sodium are presented, and about 250 ml tetrahydrofuran (THF) are added. At an internal temperature of about 40° C., 26.1 g (0.25 mol) styrene are added dropwise within about 1.5 h. The reaction starts within about 5 min after the first addition of styrene, and is weakly exothermal. Upon termination of the addition, the mixture is refluxed for 0.5 h, and upon cooling the slightly turbid solution is filtered. 0.4 g unreacted sodium are weighed back. There is obtained 294.5 g solution with a hydride hydrogen content of 4.79 mmol/g, which corresponds to a content of 37.0 g sodium dimethylaminoborohydride or a yield of 92%. The sodium dimethylaminoborohydride is present in the solution as THF complex.

EXAMPLE 2

1.9 g (48.6 mmol) potassium are presented in 150 ml THF and are mixed with 2.86 g (48.6 mmol) dimethylaminoborane by stirring. By slowly evolving hydrogen, the potassium goes into solution. After about 18 h, the reaction is terminated. From the turbid solution a potassium metal residue of 0.1 g is removed. The NMR-spectroscopic examination of the solution indicates that the dimethylaminoborane has reacted completely. The saturated tetrahydrofuran solution contains 0.36 mmol/ml potassium dimethylaminoborohydride in the form of the THF complex.

EXAMPLE 3

1.9 g (48 mmol) potassium are presented in 150 ml toluene, and 2.86 g (49 mmol) dimethylamineborane are added. There is slowly evolved gas, and a colorless precipitate is formed. After about 12 h the potassium has reacted completely. The precipitate is separated by centrifuging and decanting and dried in a vacuum. 3.8 g potassium dimethylaminoborohydride are obtained, which corresponds to a yield of 81%.

EXAMPLE 4

2.85 g (73 mmol) potassium are added to a solution of 8.4 g diisopropylamineborane in 150 ml hexane. There is noted an immediate formation of gas, and a colorless product is precipitated. In the course of 1 h a catalysis is effected, and the reaction is terminated after about 3 h. The solvent is withdrawn in a vacuum. There is left a colorless powder, which consists of potassium diisopropylaminoborohydride.

Yield: 10.5 g (94%)

EXAMPLE 5

In a 250 ml flask 2.1 g (54 mmol) potassium are presented in 150 ml toluene, and 5.3 g (54 mmol) piperidine borane are added. There is observed a moderate evolution of gas, and a colorless product is precipitated. After about 4 days the potassium has dissolved completely. The precipitate is centrifuged off, and the supernatant is discarded. The product virtually completely insoluble in toluene is washed with 200 ml toluene and dried in a vacuum. It consists of potassium piperidineborohydride, i.e. of $K[(CH_2)_5N.BH_3]$, Fp. 245° C.

Yield: 3.6 g (49%)

EXAMPLE 6

In an ice-cooled flask, 3.2 g lithium amide (140 mmol) are added by stirring to a solution 8.2 g dimethylamineborane (140 mmol) in 40 ml THF. Immediately upon adding $LiNH_2$ the solution starts to evolve gas ($NH_3$). A colorless product is precipitated. Then, stirring is continued for 12 h. To improve the filtration properties, the solution is allowed to stand for about 24 h and is then filtrated, whereupon 2.3 g of a grey, insoluble residue are obtained. The filtrate is evaporated to dryness. A colorless powder is obtained, which is identified as complex with 0.5 mol THF. 13.5 g $Li(Me_2N.BH_3).0.5THF$ are isolated, which corresponds to a yield of 96%.

EXAMPLE 7

10.61 g dimethylamineborane (180 mmol) are dissolved in 150 ml THF. 1.25 g lithium metal powder (180 mmol) are added. If the reaction does not start spontaneously (noticeable by the evolution of gas), the mixture is briefly heated to about 55° C. After 0.5 h the solution starts to foam up and gas vigorously. After another hour, the lithium is dissolved completely. The colorless to light-brown solution is liberated from insoluble matter. The filtrate is transferred to a colorless powder by distilling off the solvent. The raw product yield is 14 g (77%). The product can be dissolved in 200 ml briefly boiled toluene. After the solution was liberated from insoluble matter, the compound crystallizes out in the form of colorless blocks within two weeks at room temperature.

EXAMPLE 8

To a solution of 21.22 g (360 mmol) dimethylamineborane in 260 g THF, 2.56 g (369 mmol) lithium metal are added. To this, 19.15 g (184 mmol) styrene are added dropwise within 45 min. The reaction is exothermal. It is observed that the Li is dissolved completely, and a slightly turbid solution is formed. By NMR-spectroscopy, the complete conversion to lithium dimethylaminoborohydride, which is present as THF complex, is demonstrated. The filtered solution has the following analysis:

Li: 1.08 mmol/g, B: 1.10 mmol/g, H: 3.07 mmol/g

Yield: 81% (based on hydride hydrogen)

EXAMPLE 9

77.5 g ($\approx$371 mmol H$^-$) of the about 12.9% solution of sodium dimethylaminoborohydride prepared in accordance with Example 1 are presented in a 500 ml flask and mixed with the solution of 19,1 g (127 mmol) benzoic ether in 67 g THF at room temperature. Upon complete addition, the mixture is refluxed for 1 h and subsequently hydrolysed with 6N hydrochloric acid. During the reaction and hydrolysis a gas volume is produced which corresponds to 130 mmol hydride. The organic phase is separated, and the aqueous phase is again extracted by shaking with four times 50 ml $Et_2O$. The combined ether phases are dried with $MgSo_4$ upon neutralization with $NaHCO_3$, and the diethyl ether is distilled off in a vacuum.

Yield: 12.3 g (81%). In the raw product solution no more ester can be detected (NMR, GC).

EXAMPLE 10

1.23 g crystalline $Li(Me_2N.BH_3).0.5THF$ (12.18 mmol; from Example 7) are presented in a 100 ml flask, and 40 ml toluene are added. Then, 1.65 ml benzoic ether (16.45 mmol) are added dropwise. The solution takes on a light-yellow color. The solution (there is no suspension) is refluxed for 0.5 h. Then, the solution is hydrolyzed with 20 ml 6N HCl. There are released 200 ml $H_2$ (8.92 mmol). As product there are formed 1.4 g (82%) benzyl alcohol.

EXAMPLE 11

20 ml of a 1.13 molar solution of the THF complex of lithium dimethylaminoborohydride (22.6 mmol; from Example 8) are presented in a 50 ml flask, and 2.26 ml benzoic ether (22.5 mmol) are added. The solution immediately turns yellow. Then it is refluxed for 0.5 h. The content of the flask is transferred to a separation funnel and hydrolyzed with 40 ml 6N HCl. Subsequently, NaOH is added in such an amount until the solution is strongly basic. The aqueous solution is extracted by shaking with 40 ml diethyl ether, and the ether phase is separated. This is repeated twice with 20 ml ether. The ether phases are dried over night over $MgSO_4$. The dried solution is transferred to a flask, and the ether is distilled off in a vacuum. As product $C_6H_5CH_2OH$ is obtained.

Yield: 2.16 g (89%)

We claim:

1. A process for preparing a compound of the Formula $$M(R^1R^2N.BH_3)$$

or a complex thereof of the Formula $$M(R^1R^2N.BH_3).xL$$

wherein

M is Li, Na, K, Rb or Cs;

$R^1$ is H, an aliphatic $C_1$ to $C_5$ residue, an aromatic residue, or a cycloaliphatic residue;

$R^2$ is H, an aliphatic $C_1$ to $C_5$ residue, an aromatic residue, or a cycloaliphatic residue; or $R^1$ and $R^2$ form a common cyclic residue;

L is a dipolar aprotic solvent; and x is a numerical value from 0.1 to 5, which comprises the steps of:

(a) where the compound of the Formula $M(R^1R^2N.BH_3)$ is prepared, reacting a compound of the Formula $$R^1R^2NH.BH_3$$

with an alkali metal or an alkali metal amide in a non-polar aliphatic or aromatic solvent; or (b) where the complex of the Formula $M(R^1R^2N.BH_3).xL$ is prepared, reacting the compound of the Formula $$R^1R^2NH.BH_3$$

with an alkali metal or an alkali metal amide in the dipolar, aprotic solvent or is a mixture of the dipolar aprotic solvent and the non-polar aliphatic or aromatic solvent.

2. The process defined in claim 1 wherein according to step (a) or step (b), reaction with an alkali metal is performed in the presence of a proton acceptor.

3. The process defined in claim 2 wherein styrene is the proton acceptor.

4. The process defined in claim 1 wherein according to step (a) hexane or toluene is the non-polar aliphatic or aromatic solvent.

5. The process defined in claim 1 wherein according to step (b) an ether or a tertiary amine is the dipolar aprotic solvent.

6. The process defined in claim 5 wherein the ether is tetrahydrofuran, diethyl ether or dioxane.

7. The process defined in claim 5 wherein the tertiary amine is tetramethyl ethylenediamine.

8. The process defined in claim 1 wherein according to step (a) the compound produced is lithium dimethylaminoborohydride and wherein according to step (b) the complex produced is a complex of lithium dimethylaminoborohydride.

* * * * *